US006831736B2

(12) United States Patent
Elichai et al.

(10) Patent No.: US 6,831,736 B2
(45) Date of Patent: Dec. 14, 2004

(54) METHOD OF AND APPARATUS FOR LINE ALIGNMENT TO COMPENSATE FOR STATIC AND DYNAMIC INACCURACIES IN SCANNING

(75) Inventors: Rami Elichai, Ashqelon (IL); Gilad Schwartz, Meishar (IL); Ron Naftali, Shoham (IL); Pavel Margulis, Ashdod (IL); Igor Slobodnik, Rishon LeZion (IL)

(73) Assignee: Applied Materials Israel, Ltd., Rehovot (IL)

( * ) Notice: Subject to any disclaimer, the term of this patent is extended or adjusted under 35 U.S.C. 154(b) by 232 days.

(21) Appl. No.: 10/266,823

(22) Filed: Oct. 7, 2002

(65) Prior Publication Data

US 2004/0066506 A1 Apr. 8, 2004

(51) Int. Cl.[7] .................. G01N 21/00; G02B 26/08
(52) U.S. Cl. ............... 356/237.1; 356/399; 359/216; 250/235; 347/250
(58) Field of Search ................... 356/237.1–237.5, 356/399–401, 607, 608; 359/196–226; 347/248, 250; 250/235, 236

(56) References Cited

U.S. PATENT DOCUMENTS

| | | | | |
|---|---|---|---|---|
| 3,900,265 | A | * | 8/1975 | Merlen et al. .............. 356/431 |
| 4,065,212 | A | | 12/1977 | Belleson et al. |
| 4,243,294 | A | * | 1/1981 | Noguchi ..................... 359/218 |
| 4,268,867 | A | * | 5/1981 | Traino ........................ 358/410 |
| 4,429,218 | A | * | 1/1984 | Thomas .................. 250/214 R |
| 4,783,826 | A | * | 11/1988 | Koso .......................... 382/147 |
| 4,805,123 | A | | 2/1989 | Specht et al. |
| 4,860,374 | A | | 8/1989 | Murakami et al. |
| 4,926,489 | A | | 5/1990 | Danielson et al. |
| 4,975,626 | A | * | 12/1990 | Yagi et al. ................... 318/567 |
| 5,570,183 | A | * | 10/1996 | Wiles ......................... 356/613 |
| 5,602,937 | A | | 2/1997 | Bedrosian et al. |
| 5,619,429 | A | | 4/1997 | Aloni et al. |
| 5,644,512 | A | | 7/1997 | Chernoff et al. |
| 5,717,204 | A | | 2/1998 | Meisburger et al. |
| 5,764,793 | A | | 6/1998 | Omae et al. |
| 5,825,482 | A | | 10/1998 | Nikoonahad et al. |
| 5,825,670 | A | | 10/1998 | Chernoff et al. |
| 5,864,394 | A | | 1/1999 | Jordan, III et al. |
| 6,016,358 | A | | 1/2000 | Balamurugan |
| 6,169,602 | B1 | | 1/2001 | Taniguchi et al. |
| 6,178,257 | B1 | | 1/2001 | Alumot et al. |

FOREIGN PATENT DOCUMENTS

EP    0 919 803 A1    6/1999

* cited by examiner

*Primary Examiner*—Hoa Q. Pham
(74) *Attorney, Agent, or Firm*—Sughrue Mion PLLC

(57) ABSTRACT

In a method and apparatus for compensating for static and dynamic inaccuracies in an optical scanner used in a typical surface inspection system, the scanner may have a scanning axis and a cross-scanning axis. A surface of an inspection article is scanned along a scanning axis and a scanning axis signal is output at predetermined distances along this axis. The scanning axis signal may be used to determine a speed of relative movement between the scanner and the inspection article. A jitter signal may be output whenever the scanner deviates from the scanning axis, and this signal may be used to calculate the amount of deviation. Information, such as the speed of relative movement, scan line resolution, and a scanning axis static position error may be used to generate a scan line. A generated scan line may be shifted to compensate for a cross-scanning axis error. Utilizing this method, a scan line is generated that compensates for various scanner positioning errors, including the cross-axis and scanning axis static position errors, the scanning axis dynamic position error, and the cross-scanning axis jitter error.

32 Claims, 8 Drawing Sheets

METHOD OF AND APPARATUS FOR LINE ALIGNMENT TO COMPENSATE FOR STATIC AND DYNAMIC INACCURACIES IN SCANNING

BACKGROUND OF THE INVENTION

1. Field of the Invention

The present invention relates generally to a method and apparatus for correcting inaccuracies in an optical scanner, and more particularly, to a method and apparatus for compensating for static and dynamic inaccuracies in an optical scanner.

2. Description of the Related Art

In the fabrication of modem semiconductor integrated circuits, inspection systems are used to inspect semiconductor wafers, photomasks, reticles, and other surfaces. A typical surface inspection system detects light that is scattered, reflected, or otherwise modified from a small area of an inspected surface. In order to detect errors or anomalies, data from the inspection system, in the form of a quantity of light detected, for example, may be compared with some kind of reference data. The reference data may come from a database, from another portion of the surface being inspected, or from other suitable sources.

Erroneous detection of errors or anomalies can occur when the data for a sampled surface area is not matched correctly with reference data. One source of such errors can occur when the optical system used in scanning the inspected surface is misaligned.

FIG. 1 shows a general example of an inspection system, in which an article 10 being inspected is placed on an inspection stage 20. A light source 60, which may be a laser or any suitable light source, provides its output to an acousto-optic deflector (AOD) 70, which in turn causes a light beam 55 to be output. Control of AOD 70, which for example may be accomplished, in whole or in part, by RF generator 80 under entire or partial control of a stage control 25, causes the light beam 55 to scan across the surface of the article 10. Other types of systems for causing the light beam 55 to scan as indicated may be used.

In this type of inspection system, the light beam 55 generally moves in the direction of a first axis, while the stage 20 moves the article 10 along a second, generally perpendicular axis. Relative movement between the light beam 55 and the article 10 in these respective axes may be accomplished in any known or desired manner. For example, the light beam 55 may move, and the article 10 (or stage 20) may remain stationary; the light beam 55 may remain stationary, and the article 10 (or stage 20) may move; or both the light beam and the article (stage) may move. For purposes of the following discussion, it will be assumed that the light beam scans the surface of the article 10 along the X axis, while the inspection stage moves along the Y axis.

In FIG. 1, a stage control 25 controls movement of the stage 20 in the Y axis. AOD 70 causes the light beam 55, generated by light source 60 and under control of an RF generator 80, to scan in the direction of the X axis. The RF generator 80 communicates with stage control 25 to control the scanning of light beam 55 in accordance with the movement of the stage 20.

FIG. 2 depicts generally an ideal relative movement between the stage 20 and the light beam 55. That is, ideally, in the configuration shown, for a given article 10 being inspected, the stage 20 always has the article 10 positioned precisely on it, and always begins to move at the same point along the Y axis, while the light beam 55 always begins a scan line at the same point along the X axis. With this kind of perfect alignment, the light information produced by the scan at a given position (coordinate pair) on the article will always match the data at the corresponding coordinate pair in the reference data.

Obviously, misalignment along either the X axis or the Y axis can cause misregistration, which could be sufficient to cause scan data to be matched incorrectly with reference data. As a result, an error could be misidentified in at least one of two ways. Either the system may identify a non-existent error; or the system may fail to identify an error. Accordingly, one problem that needs to be addressed is the non-ideal nature of the (x, y) grid over which the scanning occurs.

Imperfections in the (x, y) grid can result from various problems. For example, in certain kinds of inspection stage movement systems, incremental stage movements can be sufficiently imprecise to cause misalignment, with resulting inaccuracy in the position of the stage 20 relative to the light beam 55. For example, there may be an instruction to the stage 20 to move to coordinate (1000, 1000). The units of the coordinate system may be a function $\mu$ of the resolution of the inspection system. Merely by way of example, $\mu$ may be 40 nm in one type of inspection system, so that coordinate 1000 along the Y axis is actually at a location that is 40,000 nm away from the origin along that axis. As a result, if there is an error, an instruction to move to (1000,1000) actually may result in movement to coordinate (1000, 1000+$\Delta y$), where $\Delta y$ is the amount of error. In the example just given, $\Delta y$ may have a relation to $\mu$. To correct for this kind of error, it would be desirable to be able to provide an amount of compensation for $\Delta y$, particularly as a function of $\mu$.

This type of error, which is referred to as a "static" error, may not occur in certain types of stages, such as an interferometer controlled stage. Such an error may be an inherent function of the resolution of the stage control 25.

A second type of error, resulting from scan lines starting at different positions along the X axis, is referred to as "dynamic" error, because the amount of error can vary from scan to scan. One version of this dynamic error phenomenon is known as "jitter". To compensate for jitter, it is necessary to monitor the starting position of the light beam along the Y axis, and provide appropriate compensation at the start of each scan line. FIG. 3 shows an example of different degrees of jitter. To compensate for jitter, the starting position for each scan line should be normalized to a position that is an amount $\Delta x_0$ away from the Y-axis. For successive scans at times $t_1$, $t_2$, and $t_3$, the jitter adjustment would be $dx_1$, $dx_2$, and $dx_3$, respectively.

In order to correct for the kinds of static and dynamic error just described, it would be desirable to provide an approach which facilitates starting both the initial movement of the stage, and each scan line, at the same location every time.

One way of compensating for the foregoing types of misalignments and positioning errors is known as registration. In one such registration method, a scanned image is compared to a reference image. During this comparison, the scanned and reference images are aligned, to determine the existence of a positioning error. If differences between the scanned and reference images are detected during the comparison, then compensating factors may be determined.

In the kind of registration system just described, the reference image typically is obtained from a predetermined location on a scanning surface. Other systems may generate a reference image by utilizing a previously scanned image, or even by averaging a number of previously scanned images.

One drawback of the registration method is that registration accuracy relies heavily on the quality of the scanned images. As a result, if either the scanned image or the reference image is inaccurate, the errors detected as a result of the comparison will be incorrect. It can be appreciated readily that the problem will be even worse if both the scanned image and the reference image are inaccurate.

It would be desirable to provide a system that compensates for misalignment without the need for image comparison techniques such as the just-described registration method. It also would be desirable to provide accurate scanner misalignment correction without having to rely on the accuracy of sample or reference images.

SUMMARY OF THE INVENTION

In accordance with this and other aspects of the present invention, a method is provided that compensates for one or more sources of a scanner's line alignment error. A typical surface inspection system may have a scanner with a scanning axis and a cross-scanning axis. In accordance with one aspect of the invention, when scanning a surface of an inspection object, a scanning axis signal may be output at predetermined distances along the scanning axis. The scanning axis signal may be used to determine the scanner's speed.

Also in accordance with one aspect of the invention, the inspection system may be configured to output a jitter signal whenever the scanner deviates from the scanning axis. The jitter signal, which in one embodiment may take the form of a count signal, may be used to calculate the distance that the scanner deviates from the scanning axis.

Information such as the scanner's speed, scan line resolution, and a scanning axis static position error may be used to generate a scan line that compensates for a scanning axis error. The generated scan line also may be shifted to compensate for a cross-scanning axis error based on the scanner's jitter signal and a cross-scanning static position error.

In accordance with another aspect of the present invention, there may be a calibration session, during which a predefined grid on an inspection object may be scanned to determine a scanning axis static position error and a cross-scan line static position error for each point on the grid. Each of these errors may be loaded into respective static position error correction tables.

In accordance with another aspect of the present invention, an elapsed time between two consecutive outputted scanning axis signals may be measured to calculate the scanner's speed.

In accordance with yet another aspect of the present invention, a cross-scanning axis error may be calculated by combining scanner deviation with cross-scanning static position error.

Another aspect of the present invention enables the system to determine the scanner's resolution, which may be based on a variety of factors such as the scanner's speed, or the inspection object's surface structure or material composition.

Still another aspect of the present invention provides a system that may scan a variety of different types of inspection objects, such as semiconductor wafers, photomasks, reticles, flat panel displays, and biological materials.

In accordance with still yet another aspect of the present invention, a scanning process may continue until the scanning pass is completed.

These and other aspects, features and advantages of the present invention will become more apparent upon consideration of the following description of embodiments of the present invention taken in conjunction with the accompanying drawings.

DETAILED DESCRIPTION OF EMBODIMENTS

The scanner misalignment correction system of the present invention may be utilized in a variety of different surface inspection systems. One example of a surface inspection system that may utilize the present invention is the COMPASS™ system by Applied Materials, Inc., the assignee of the present invention.

A surface inspection system utilizing the present invention typically comprises a scanner having two orthogonal motion axes, which will be referred to as a scanning axis and a cross-scanning axis. For ease of reference, the Y-axis will be referred to as the scanning axis and the X-axis will be referred to as the cross-scanning axis. However, the particular nomenclature is not critical to the invention.

During a typical scanning session, the scanner will scan an inspection surface by providing relative movement between the scanner and the inspection surface. Whether the scanner moves, or the inspection surface moves, or both the scanner and the inspection surface move, is not critical to the invention. What matters is that there is relative movement between the two. In the following discussion, if movement of only one of the scanner or the inspection system is mentioned, it is to be understood that relative movement (including movement of both) is contemplated.

In accordance with the present invention, a scanner may be configured with signal output devices, for example, to generate identifiable signals when the scanner passes predetermined points along either the scanning or the cross-scanning axis. A scanner may be configured to generate one type of signal when the scanner is moved along the X-axis, and another type of signal when the scanner moves along the Y-axis. In the following discussion these signals will be referred to as X-count and Y-cross-zero, denoting scanner movement along the X and Y axes, respectively.

In accordance with the present invention, scanner line misalignment correction is provided using a line alignment method to correct for as many as three kinds of scanner errors: a scanner's static position error; its dynamic position error; and its jitter error. In the present scanning system, a typical scanning session is performed by providing relative movement for the scanner along its scanning axis (e.g., Y-axis), while a cross-scan is performed by providing relative movement for the scanner along its cross-scanning axis (e.g., X-axis).

Also, merely by way of example, the following description of embodiments of the invention may refer to a surface inspection system for inspecting a surface of a semiconductor wafer. However, it is to be understood that the present invention is not so limited, but instead is suitable for inspection of other types of articles, such as photomasks, reticles, flat panel displays, biological substances (e.g., DNA), and the like.

Overview of Scanner Line Alignment System

Figure 4:
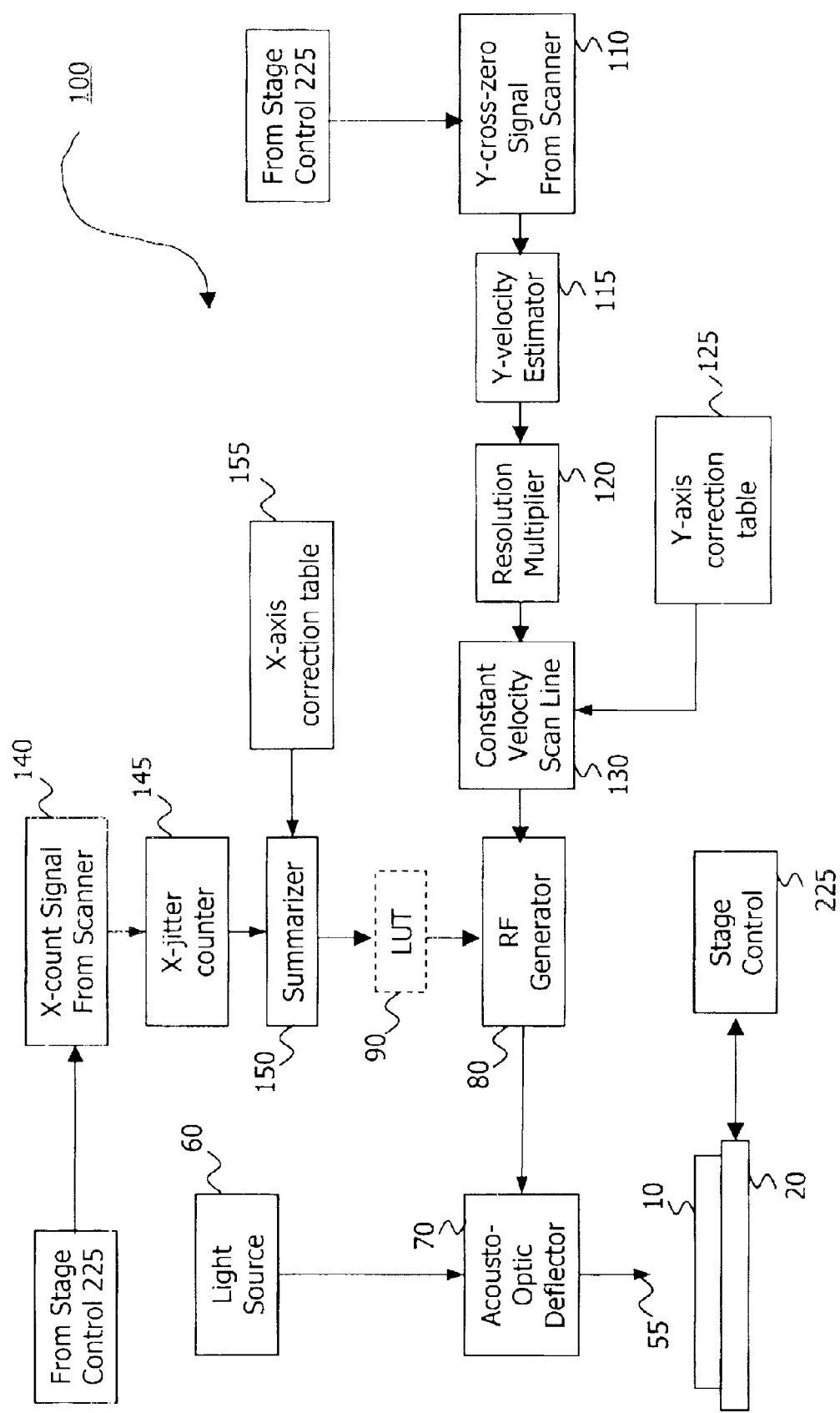
FIG. 4 is a block diagram illustrating an overview of several of the major modules of a system that compensates for scanner line alignment inaccuracies.

FIG. 4 is a block diagram providing an overview of some of the major components of the inventive system 100 that may be utilized to correct scanner line misalignment. The relative relationship of each of these components, along with a brief description of their respective functions now will be discussed.

In FIG. 4, stage control 225 is coupled to stage 20, and provides motion control signals to the stage 20. In one embodiment, stage control 225 not only provides signals to stage 20, but also receives signals from it. In another embodiment, stage control 225 also can provide Y-cross-zero signals to Y-cross-zero signal block 110. However, this is not required, and the block 110 can receive those signals in a variety of ways known to ordinarily skilled artisans.

As described earlier, AOD 70 is controlled by signals from RF generator 80. As seen in FIG. 4, RF generator 80 receives inputs from a constant velocity scan line block 130. This block 130 in turn receives input from the scanner via a Y-cross-zero signal block 110, through a Y-velocity estimator 115 and a resolution multiplier 120. The resolution multiplier 120 sets the smallest amount of scanner motion that is to be acknowledged as motion. Together, these blocks enable the stage to move such that it starts at a consistent position at each scan line. Block 130 also receives an input from a Y-axis correction table 125.

In another embodiment, RF generator 80 can receive inputs from a look-up table (LUT) 90, which is located between the RF generator 80 and a summarizer 150, which will be discussed below in conjunction with the X-axis correction scheme. In yet another embodiment, RF generator 80 receives input comprising X-count information from block 140, via a jitter counter 145, and a summarizer 150. The summarizer 150 also may receive input from an X-axis correction table 155, where LUT 90 is accessed based on an output of summarizer 150. This overall combination enables adjustment of the initial position of the light beam 55 at the start of each scan line.

A scanning system that utilizes the scan line alignment method of the present invention may be configured so that it outputs an Y-cross-zero signal at various points along a scanning path. In one embodiment, a scanner may be configured so that it outputs an Y-cross-zero signal at each of a series of predetermined distances along the scanner's scanning path (e.g., Y-axis). During a typical scanning process, the scanner may generate a series of Y-cross-zero signals that correspond to a series of distances along the scanning path.

Similarly, the scanner also may be configured to output an X-count signal whenever the scanner deviates from an intended scanning path. As discussed earlier, this kind of deviation is known as jitter. During a typical scanning process along the Y-axis, optimally the scanner would not deviate from the intended scanning axis (e.g., Y-axis). However, scanning systems are susceptible to internal and external forces that may affect the actual scanning process. As such, a typical scanner will experience jitter (i.e., scanner fluctuations about an intended scanning axis) during scanning.

X-count signals may be output in response to an elapsed period of time during which no Y-cross-zero signals are detected. Other suitable sources of X-count signals will be apparent to ordinarily skilled artisans. In one embodiment, X-count signals may come from stage control 225 which receives corresponding information from stage 20, but this is not required.

Detected X-count signals may be communicated to the X-jitter counter 145, for example, so that an X-axis jitter error may be calculated. The calculation may be based, for example, on deviation of an X-count from an expected value. The expected value may be zero, or any other suitable value. For example, it may be a nonzero value in order to accommodate tolerances in deviation. X-axis jitter error is defined as the distance that the scanner has deviated from the intended scanning axis (e.g., Y-axis).

In addition to measuring scanner jitter, the respective times that the Y-cross-zero and X-count signals are outputted may be monitored to provide the system with information that may be used to perform additional calculations, such as the scanner's speed, as well as to identify the scanner's location along the scanning or cross-scanning axes. For example, if a scanner's speed is to be calculated, the system may monitor the timing of the outputted signals and then correlate them with the distances that triggered the signals. Typically, the scanner's speed is calculated by a Y-velocity estimator 115. One technique for calculating the scanner's speed is to measure the elapsed time between two consecutive Y-cross-zero signals. As would be apparent to those skilled in the art, the signals do not have to be consecutive, so long as relevant time and distance information are available from which to make the speed calculation.

The source of the Y-cross-zero signals may be any appropriate source. In one embodiment, these signals may come from stage control 225, which receives corresponding information from stage 20. However, this is not required.

Similarly to calculating the scanner's speed, a scanner's location also may be calculated by monitoring the outputted signals. Since each of the outputted signals may be correlated to a particular distance along the scanning or the cross-scanning axis, the location of the scanner may be established by associating the detected signals with the respective distances that triggered the signals.

Typically, signal triggering distances along each of the X and Y axes may be anywhere from 2 to 20 microns; however, shorter or longer distances also may be used. Accordingly, it is to be understood that the present invention is not limited to a specific distance or range of distances that trigger the X-count and Y-cross-zero signals.

In addition to calculating the scanner's speed, an appropriate scan line resolution also may be determined. One method of determining scan line resolution is to obtain this information from a resolution multiplier 120. As will be discussed in detail with respect to FIG. 6, the resolution multiplier 120 may be populated with scan line resolution data during a tuning process.

FIG. 4 further shows a constant velocity scan line module 130 in communication with the resolution multiplier 120 and a Y-axis correction table 125. The constant velocity scan line module 130 may be configured to utilize data, such as the scanner's speed, scan line resolution, as well as the Y-axis static position error when triggering the generation of a scan line. As will be discussed in more detail below, the constant velocity scan line module 130 acts as a signal counter, which can either advance or delay the timing of generation of a scan line. The ability to advance or delay the generation of a scan line permits the system to compensate for any Y-axis error that may be present in the scanner. In this regard, it may be noted again that stage control 225 provides instructions to move stage 20. The operation of RF generator 80 may be controlled suitably by constant velocity scan line module 130 to make necessary Y-axis corrections, by either advancing or delaying the generation of a new scan line.

Similarly to the outputted Y-cross-zero signal, an X-count signal may be outputted from a scanning system. The X-count signal may be communicated to an X-jitter counter 145, in which the X-jitter error may be calculated. The calculated X-jitter error is then communicated to a summarizer 150 which utilizes the calculated X-jitter error, along with any data located in X-axis correction table 155 (i.e., the X-axis static position error), to define the X-axis error. The X-axis error may be used to correct scanner line misalignment along the X-axis. In one embodiment, the output of summarizer 150 is used as an input to access LUT 90, which in turn provides signals to RF generator 80. However, both the LUT and summarizer 150 may provide input to the RF generator 80. Together, the values from summarizer 150 and/or LUT 90 provide appropriate control to RF generator 80 to enable generation of an aligned scan line that compensates for the detected X-jitter error and the X-axis static position error.

Figure 5:
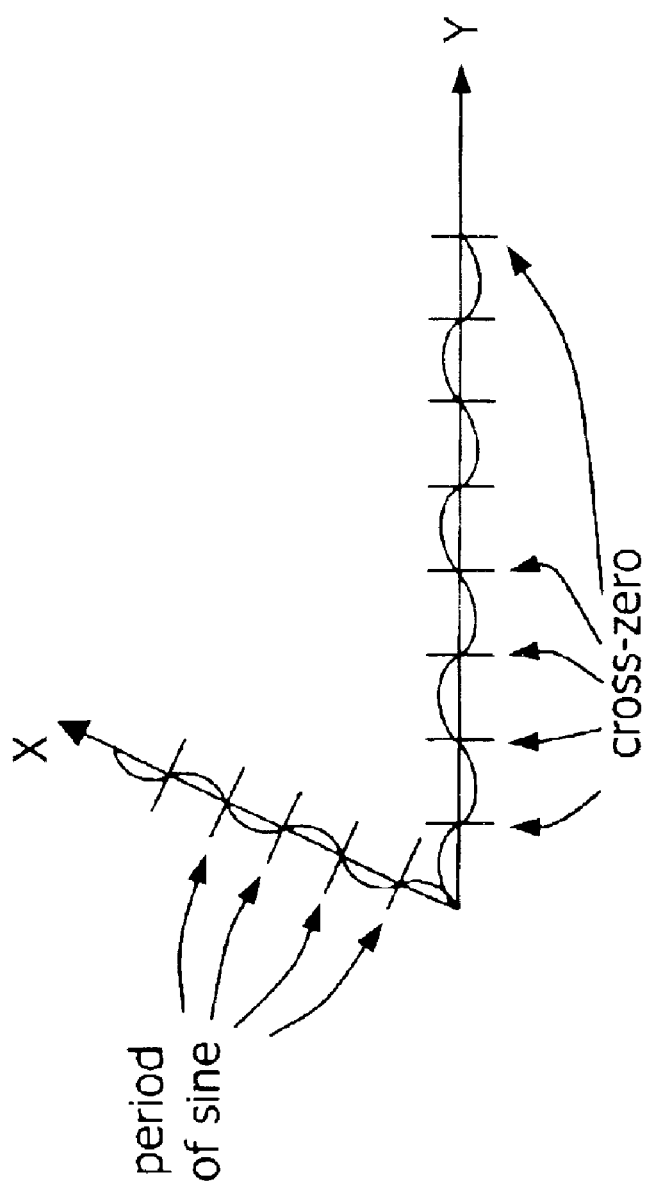
FIG. 5 is a diagram illustrating one approach to obtaining accurate distance measurements along the scanning axis.

FIG. 5 illustrates one approach to obtaining accurate distance measurements along the scanning direction. The X-axis and Y-axis of the stage may be coated with a material that, when illuminated and then scanned, provides a reflection signal having an amplitude which, assuming constant movement in the scanning direction, will resemble a sine wave with appropriate periodicity. In one embodiment, the period may be 40 nm, though the actual periodicity is not critical to the invention.

Reflection signals may be generated at every zero-crossing point along the scanning direction. These signals need not be generated that frequently, but for example may be generated at some other periodicity of occurrence of zero-crossing points. However, there is some relationship between this periodicity, and the resulting accuracy. There is an assumption that a zero-crossing point will be less noisy than other points along the scanning direction. In this manner, accurate distance measurements along the scanning direction may be based on the distance between two consecutive zero crossing points. The Y-cross-zero signal from the scanner, then, at block 110 in FIG. 4, is provided to Y-velocity estimator block 115.

Processing Flow for Correcting Scan Line Misalignment

Figure 6:
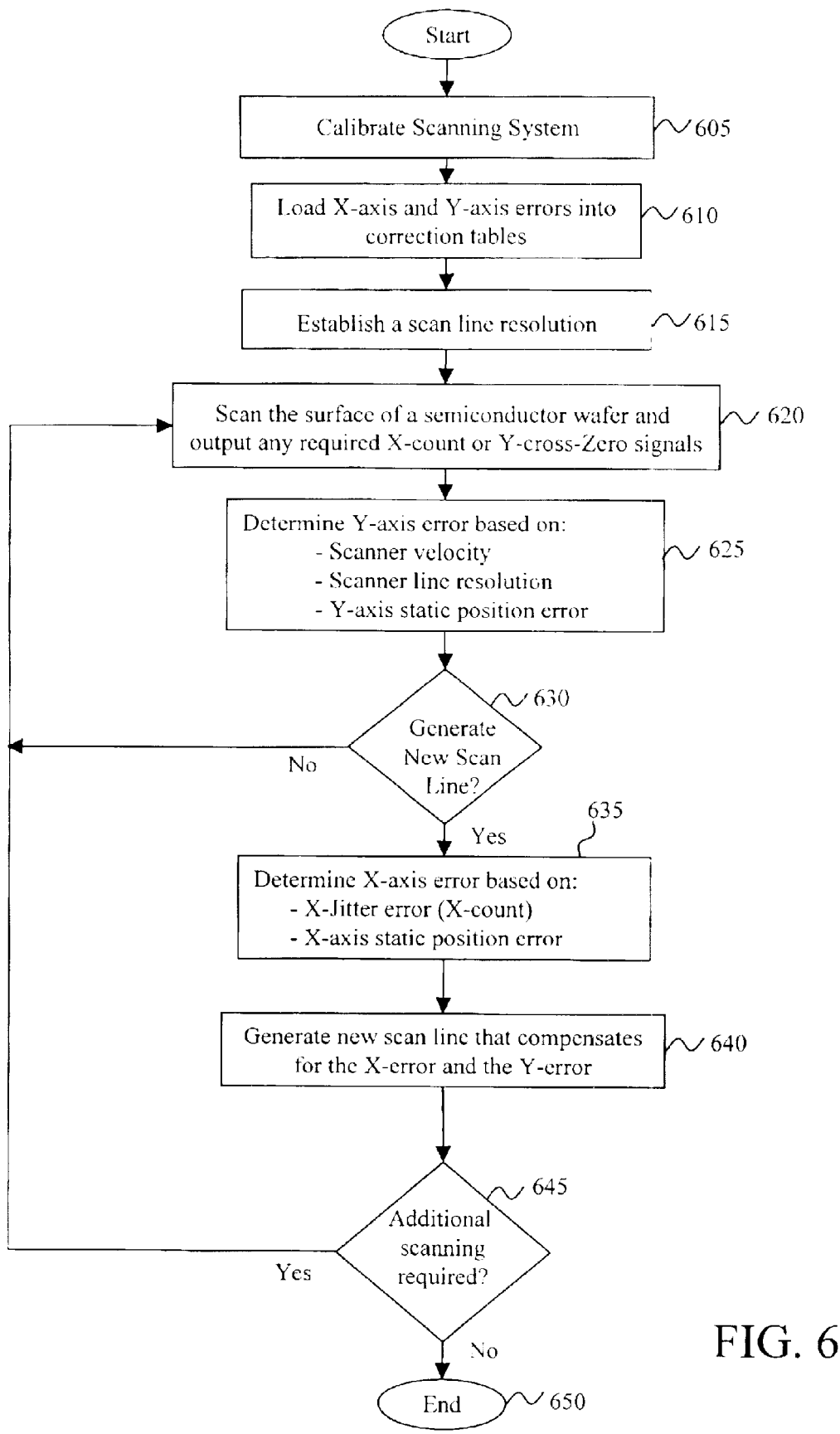
FIG. 6 is a flowchart showing an exemplary method for correcting scanner line alignment inaccuracies.

FIG. 6 shows an exemplary processing flow for correcting scan line misalignment.

Figure 7:
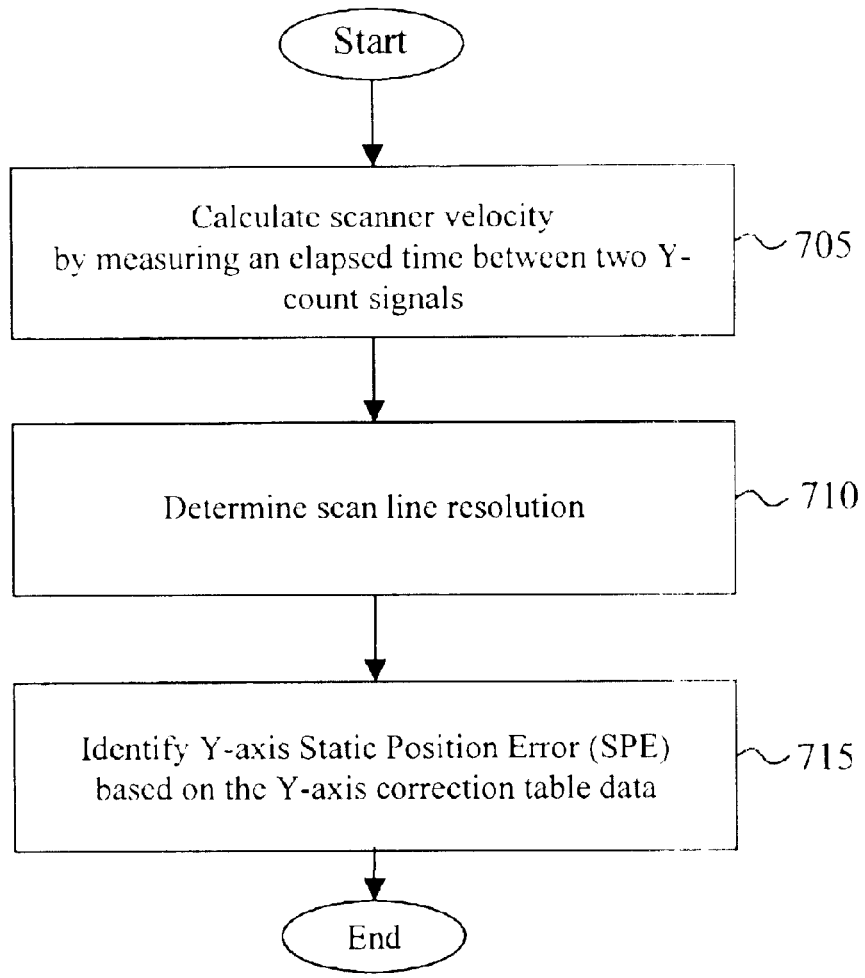
FIG. 7 is a flowchart showing an exemplary method for calculating scanning axis error.
Figure 8:
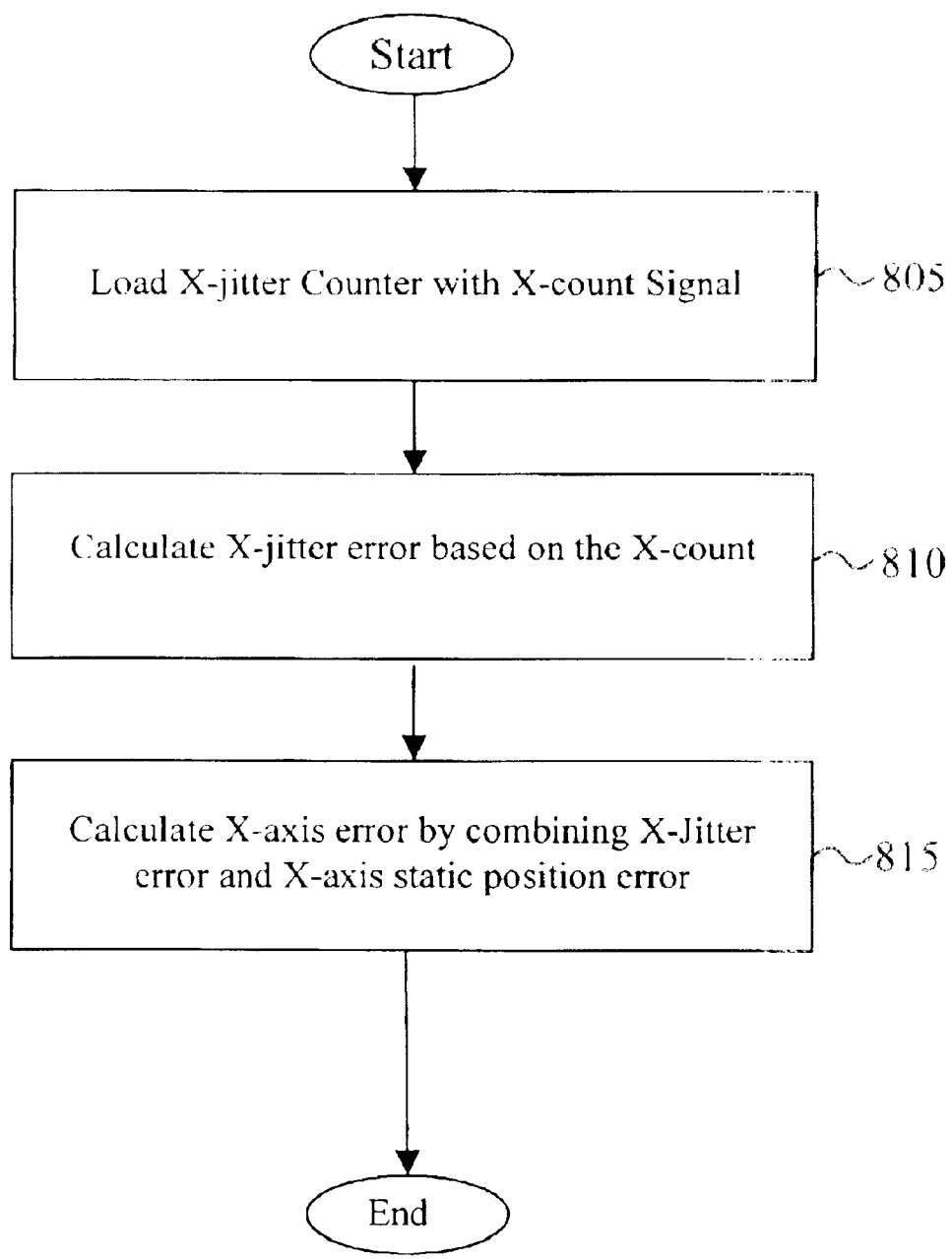
FIG. 8 is a flowchart showing an exemplary method for calculating cross-scanning axis error.

Several of the steps shown in FIG. 6 relate to operations that may be performed as illustrated in FIGS. 7 and 8.

In particular, the Y-axis error calculation shown in FIG. 6, step 625, may be performed by the method illustrated in FIG. 7. Likewise, the X-axis error calculation shown in FIG. 6, step 635, may be accomplished by performing the operations illustrated in FIG. 8. As such, the description of an exemplary processing flow for correcting a scanner line misalignment will be described with reference to FIG. 6, with reference made to the other figures when necessary.

Looking at the first step in FIG. 6, a calibration session is performed to calculate a static position error for both the X and Y axes (Step 605). One method for performing a calibration session is to scan a predefined grid of an inspection surface. The calibration grid typically will contain predefined points having X and Y coordinates. During a calibration session, the scanner's alignment errors for each point on the grid (i.e., each specific X and Y coordinate) may be identified. The scanner's alignment errors for each point on the grid may be referred to as the X-axis error and the Y-axis error, respectively.

Once the X-axis errors and the Y-axis errors have been calculated, they may be loaded into their respective correction tables (e.g., X-axis error correction table 155 and Y-axis error correction table 125) (Step 610). The data stored in these correction tables may be made available to the system to correct a scanner's static position error.

Typically, the calibration session will occur as part of the scanning system's installation process. However, a calibration session may be performed whenever it may become necessary, for example, in the course of maintenance. Thus, the calibration session does not necessarily have to be performed every time scanning is to be performed. Operational misalignments can occur during the useful life of scanning systems such as the one in which the inventive system may be implemented. Accordingly, periodic calibration may be desirable, but is not essential. There are a variety of calibration systems and methods which will be known to those of ordinary skill in the art. Any of these may be utilized by the present invention, and accordingly the calibration session need not be described further here.

Once the error data has been stored in the appropriate correction table, that aspect of the calibration session is concluded, and control is passed back to FIG. 6, step 615. At step 615, a desired scan line resolution may be determined, for example, during a tuning or calibration process. Data obtained during this process may be used to populate a resolution multiplier 120, for example. A number of different factors may be considered when selecting a scan line resolution. These factors include, for example, the type of material inspected, the size of surface features, and die size, as well as scanner speed. It is to be understood that the present invention does not rely upon any specific scan line resolution and may accommodate most any resolution.

Scan line resolution typically will be adjusted to meet the requirements of each inspection session so that an inspection surface's unique characteristics (e.g., surface material, exposed features, etc.) may be accommodated. However, once the resolution is determined, typically it will remain unchanged during the entire scanning process (e.g., the scanning of an entire wafer). In a typical configuration, the resolution is determined in a system operation by an operator; however, some or all of this process can be automated easily.

After the system has been calibrated and the scanner resolution has been determined, a surface scanning process may be initiated. Referring still to FIG. 6, a surface scanning process may be initiated by moving the scanner a predetermined distance along its scanning axis (Step 610). Typically, this will result in moving the scanner along the Y-axis. However, one of ordinary skill will realize that the present invention may be configured easily to provide scanning along the X-axis.

Once the scanner has traveled a predetermined distance, the scanning system outputs an appropriate signal (Step 620). As described previously, this signal indicates that the scanner has reached a particular distance along the scanning axis. The outputted signal will be referred to as a Y-cross-zero signal.

In the next step, the outputted Y-cross-zero signal is used to trigger a correction process that determines the scanner's dynamic position error (Step 625). An exemplary method for determining a scanner's Y-axis error (i.e., Y-axis dynamic position error and Y-axis static position error) is shown in FIG. 7.

In the present invention, a scanner's Y-axis error may be determined, and therefore corrected, by identifying one or more of the scanner's speed, the scan line resolution, and the Y-axis static position error.

Referring now to FIG. 7, step 705, the scanner's speed may be calculated using, for example, the Y-velocity estimator 115. As previously described, the scanner's speed may be calculated by monitoring the timing of the outputted Y-cross-zero signals and then correlating them with the distances that triggered these signals. For example, the elapsed time between two consecutive Y-count signals, as well as the scanning distance (i.e., the amount of relative movement between the scanner and the scanned article between successive Y-cross-zero signal outputs) may be used for the speed calculation. Again, the signals need not be consecutive.

In the next step, the system determines the scan line resolution that is to be utilized during scan line generation (Step 710). In the present invention, scan line resolution may be determined using data that was previously supplied to the resolution multiplier 120 during a system tuning process.

In the next step, the Y-axis static position error is identified using, for example, the data stored in the Y-axis correction table 125 (Step 715). As described above, the Y-axis correction table may be populated with Y-axis static position error data during a previously performed scanner calibration session.

Figure 1:
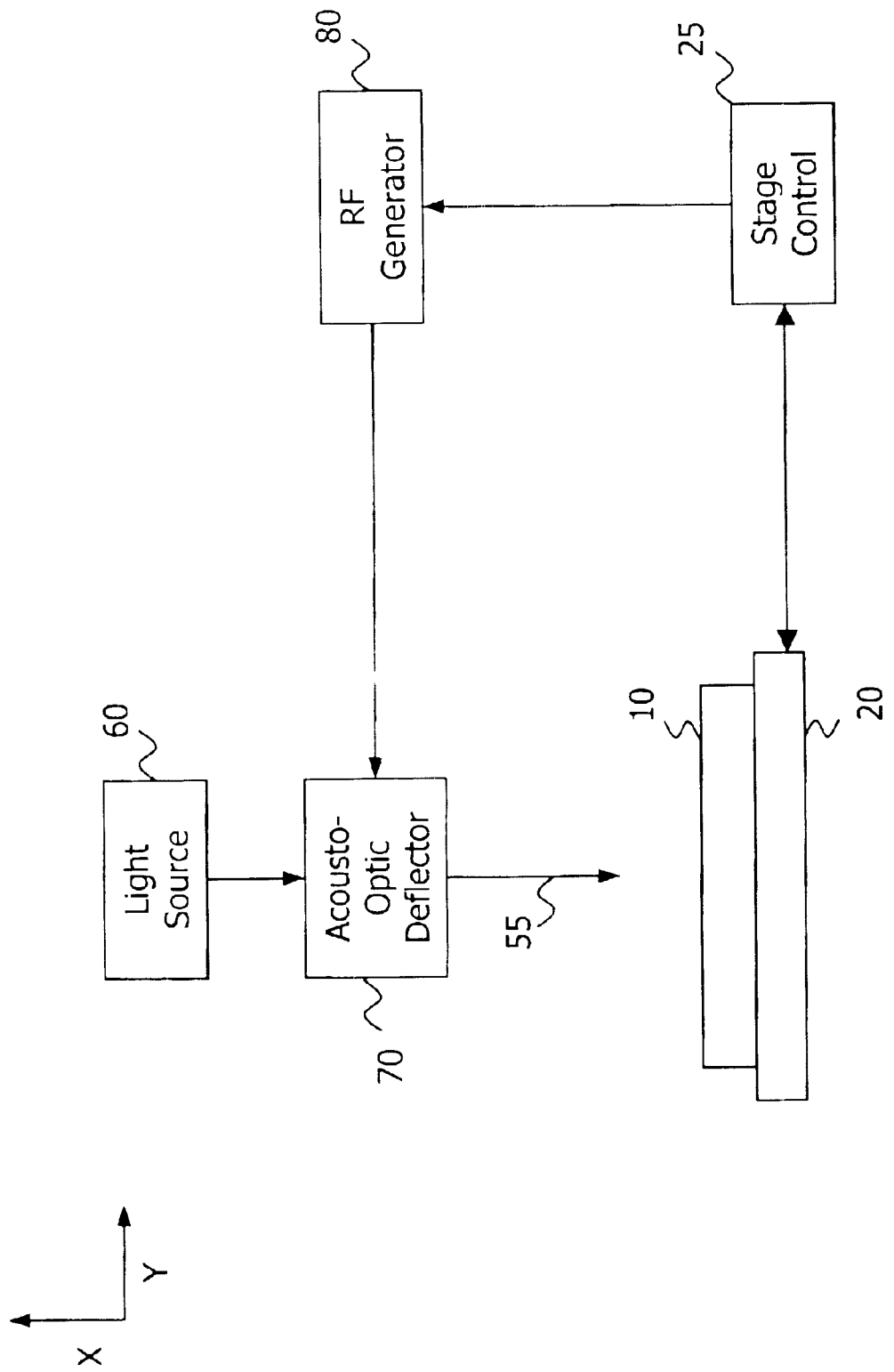
FIG. 1 is an overview of an exemplary scanning and inspection system to which the present invention may be applied.
Figure 2:
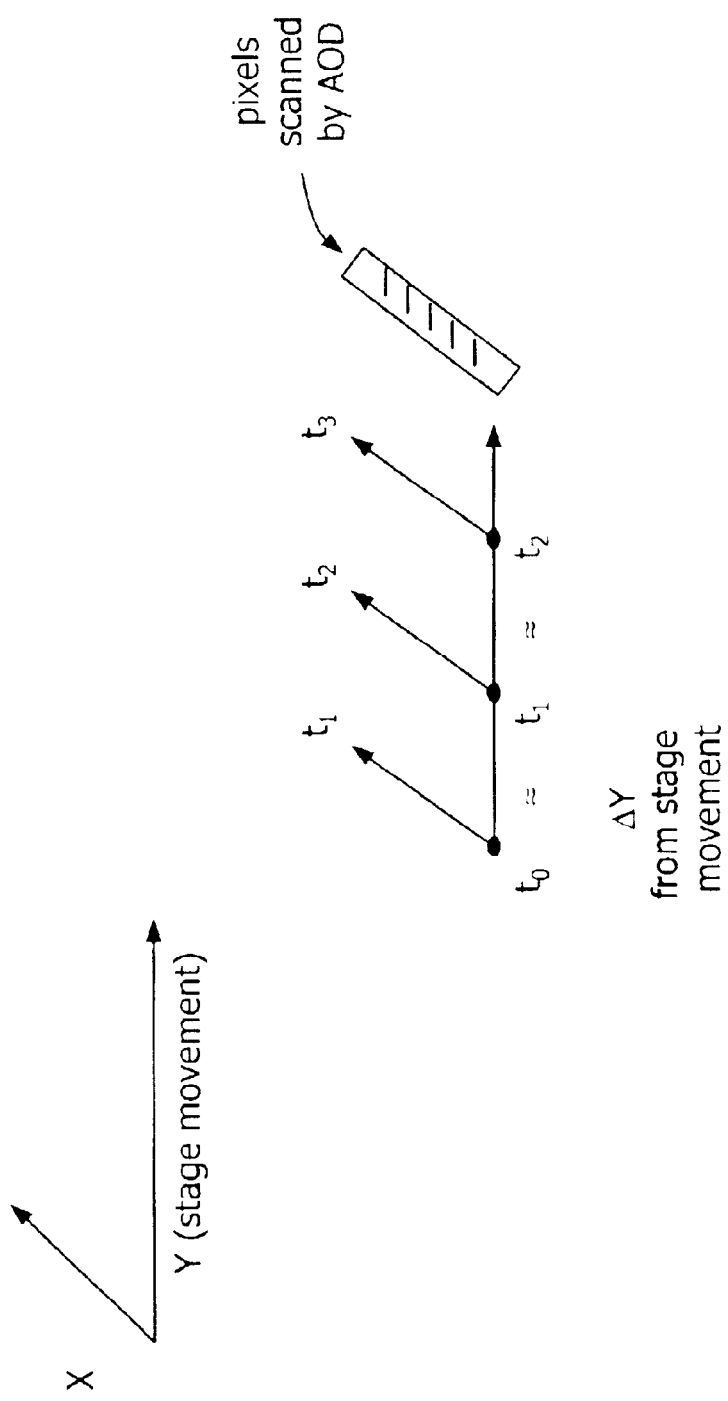
FIG. 2 is a diagram illustrating ideal movement of a scanning beam.
Figure 3:
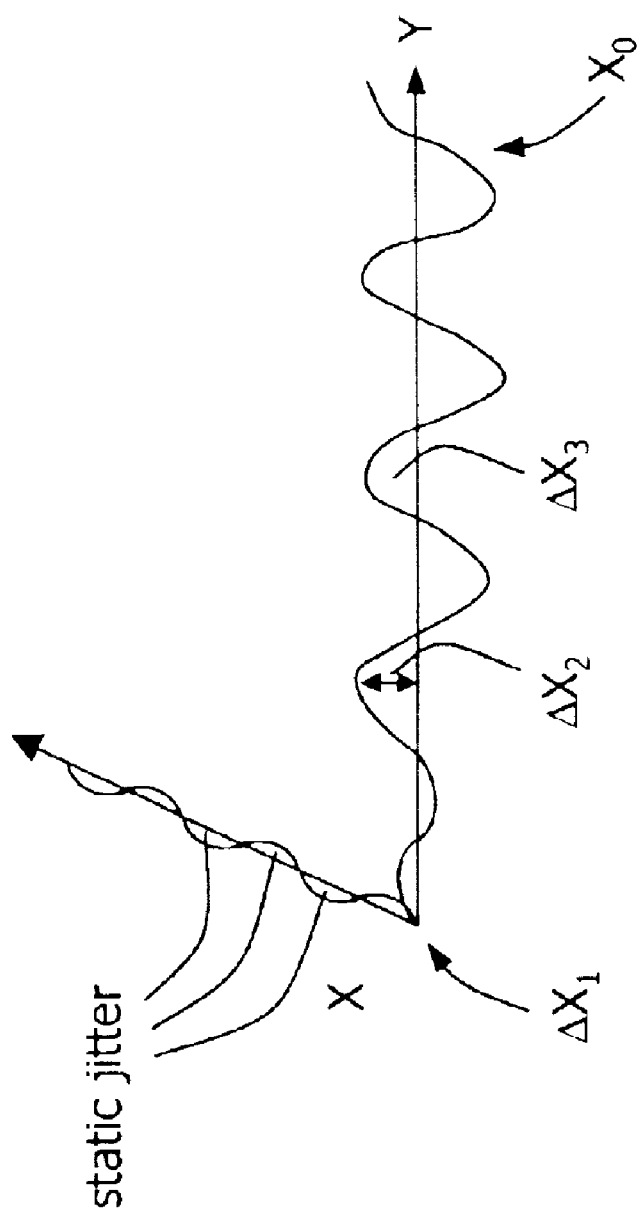
FIG. 3 is a diagram illustrating one type of jitter.

Referring back to FIG. 6, a determination is made as to whether a new scan line is to be generated (Step 630). To accomplish this, information such as the identified scanner speed, scan line resolution, as well as the Y-axis static position error, may be communicated to the constant velocity scan line module 130 (FIG. 1).

The constant velocity scan line module 130 acts as a signal counter, counting the number of detected Y-cross-zero signals. The generation of a new scan line may be triggered whenever a particular number of Y-cross-zero signals has been counted. In one embodiment, once a new scan line has been triggered (i.e., a desired number of Y-cross-zero counts has been counted), the constant velocity scan line module 130, for example, may indicate the need for a new scan line.

By increasing or decreasing the number of Y-cross-zero signals that triggers a scan line generation, the present system can advance or delay the timing of generation of a new scan line. That is, increasing the desired number of Y-cross-zero signals may result in generating a new scan line later. On the other hand, decreasing the desired number of Y-cross-zero signals may result in generating a new scan line sooner.

The constant velocity scan line module 130 typically utilizes available information, such as the identified scanner speed, scan line resolution, and Y-axis static position error, when determining whether to advance or delay the generation of a new line. The ability to control the timing of when a new scan line is generated permits the system to compensate for any Y-axis error (e.g., Y-axis-dynamic positioning error, Y-axis static positioning error) that may be present.

Accordingly, if a required number of signals has not been reached, it is not time to generate a new scan line, and so control flows back to step 620 and the scanner may continue with the scanning process. On the other hand, if a required number of signals has been detected, then the system may use this detection to trigger the generation of a new scan line.

At step 635, the X-axis error may be determined next. An exemplary method for calculating the X-axis error is shown in FIG. 8.

In the present invention, a scanner's X-axis error may be determined, and therefore corrected, by utilizing data, such as the X-jitter error and the X-axis static position error. As described previously, a scanning system may be configured to generate X-count signals whenever scanner jitter is detected (i.e., scanner fluctuations about the Y-axis).

Looking now at FIG. 8, an X-jitter counter 145 first may be loaded with a detected X-count signal (Step 805). In instances where scanner jitter has occurred, the X-count signal may contain data that can be utilized to calculate the jitter error (e.g., the distance that the scanner deviates from the Y-axis) (Step 810). On the other hand, the lack of an X-count signal may indicate that no scanner jitter is present, and that the scanner has not deviated from its intended scanning course (e.g., Y-axis). To indicate the absence of scanner jitter, the X-jitter counter may be loaded with a nil value, for example.

In the next step, the summarizer 150 calculates an X-axis error by adding any detected X-jitter error to the X-axis static position error (Step 815). Similarly to the Y-axis static position error, the X-axis static position error is obtained from the X-axis error correction table 155 generated from the previously described calibration session.

Looking again at step 815, whenever X-axis static position error is present, but no X-jitter has occurred, the X-axis error will reflect the X-axis static position error. Likewise, whenever X-jitter error is present, but no X-axis static position error has been detected (i.e., the X-axis error correction table 155 does not contain data indicating that an error is present), the X-axis error will reflect the X-jitter error.

However, since a typical scanning process will have both X-axis static position error and X-jitter error, a typical X-axis error will reflect a combination of both types of X-axis alignment errors (i.e., the X-jitter and X-axis static position errors).

Referring back to FIG. 6, processing flow now has reached step 640. It is to be understood that at this point in the processing, the data reflecting the Y-axis error, as well as the data reflecting the X-axis error, have been calculated. Accordingly, the necessary calculations now may be performed to generate a properly aligned scan line.

For example, the data obtained from the summarizer 150 (e.g. X-axis error) may be used to determine the extent to which a generated scan line requires shifting. More particularly, the appropriate distance that a generated scan line is to be shifted may be calculated to compensate for the identified X-jitter error, as well as any X-axis static position error that may be present.

Once the shifting requirements have been determined, a new scan line is generated that compensates for the scanner's positioning errors (i.e., X and Y axes static position errors, Y-axis dynamic position error, and X-jitter errors).

Next, after the new scan line has been triggered, the system may determine whether any additional scanning is required (Step 645). If additional scanning is required, then control flows back to step 620. On the other hand, where no additional scanning is required (e.g., the scanner is at the end of a scanning pass), the scanner line alignment process may be terminated (Step 650).

In the flow shown in FIG. 6, Y-axis error is determined first, followed by X-axis error. However, obviously the sequence is not critical. The X-axis error could be determined first, followed by the Y-axis error. These errors also could be determined in parallel.

While the invention has been described in detail with reference to disclosed embodiments, various modifications within the scope and spirit of the invention will be apparent to those of working skill in this technological field. Therefore, the invention properly is to be construed with reference to the appended claims.

What is claimed is:

1. A method for compensating for a line alignment error in a surface inspection system having a scanner with a scanning axis and a cross-scanning axis, said method comprising:
   scanning a surface of an inspection article by providing relative movement between a light beam in said scanner and said inspection article;
   determining a speed of said relative movement;
   producing a jitter signal in response to a deviation of a starting point of a scan path of said light beam from said scanning axis;
   generating a new scan line to compensate for a scanning axis error based on one or more of said speed of relative movement, a scan line resolution, and a scanning axis static position error; and
   shifting said new scan line to compensate for a cross-scanning axis error based on said jitter signal, and a cross-scanning axis static position error.

2. The method according to claim 1, said method further comprising:
   scanning a predefined grid on said inspection article to determine said scanning axis static position error and said cross-scanning axis static position error for each point on said predefined grid; and
   loading each of said scanning axis static position error and said cross-scanning axis static position error into one or more static position error correction tables.

3. The method according to claim 2, wherein said jitter signal corresponds to a number of counts during a time when said starting point of scan path deviates from said scanning axis.

4. The method according to claim 3, wherein said number of counts is compared to a predetermined count, with the result indicating an error in said starting point of said scan path requiring correction.

5. The method according to claim 4, wherein said predetermined count is zero.

6. The method according to claim 4, wherein said predetermined count is such that, to correct said error in said starting point, a normalized correction value is provided so as to normalize a correct starting point for said scan path, corresponding to a predetermined distance from said scanning axis.

7. The method according to claim 4, wherein said cross-scanning axis error is compensated for based on a combination of said result with a corresponding entry from one of said one or more static position error correction tables.

8. The method according to claim 1, wherein said determining said speed of relative movement comprises:
   measuring an elapsed time between two scanning axis signals; and
   calculating said speed of relative movement based on said elapsed time.

9. The method according to claim 8, wherein said two scanning axis signals are consecutive.

10. The method according to claim 8, wherein said scanning axis signals are signals produced as a result of said light beam crossing said scanning axis.

11. The method according to claim 1, wherein said scan line resolution is determined based on at least one factor selected from the group consisting of said speed of relative movement, a surface structure of said inspection article, and a surface material of said inspection article.

12. The method according to claim 1, wherein said inspection article is selected from the group consisting of a semiconductor wafer, a photomask, a reticle, a flat panel display, and a biological material.

13. The method according to claim 1, further comprising delaying said new scan line generation based on said scanning axis error.

14. The method according to claim 1, further comprising advancing said new scan line generation based on said scanning axis error.

15. Apparatus for compensating a scanner's line alignment error in a surface inspection system, said apparatus comprising:
   a scanner having a scanning axis and a cross-scanning axis;
   a controller for compensating for said line alignment error, said compensating being performed by a method comprising:
      scanning a surface of an inspection article along said scanning axis;
      determining a speed of relative movement between said scanner and said inspection article along a scan path;
      outputting a jitter signal in response to a deviation of said scan path from said scanning axis;
      generating a new scan line that compensates for a scanning axis error based on said speed of relative movement, a scan line resolution, and a scanning axis static position error; and
      shifting said new scan line to compensate for a cross-scanning axis error based on said jitter signal, and a cross-scanning axis static position error.

16. The system according to claim 15, said system further comprising:
   a predefined grid on said inspection article, wherein said scanner scans a predefined grid to determine a scanning axis static position error and a cross-scanning axis static position error for each point on said predefined grid, and wherein said scanning axis static position errors and said cross-scanning axis static position errors are loaded into respective static position error correction tables.

17. The system according to claim 16, wherein said jitter signal corresponds to a number of counts during a time when said scan path deviates from said scanning axis.

18. The system according to claim 17, wherein said number of counts is compared to a predetermined count, with the result indicating an error in said scan path that needs correction.

19. The system according to claim 18, wherein said predetermined count is zero.

20. The system according to claim 18, wherein said predetermined count is such that, to correct said error in said starting point, a normalized correction value is provided so as to normalize a correct starting point for said scan path, corresponding to a predetermined distance from said scanning axis.

21. The system according to claim 18, wherein said cross-scanning axis error is compensated for based on a combination of said result with a corresponding entry from at least one of said static position error correction tables.

22. The system according to claim 16, wherein said inspection article is selected from the group consisting of a semiconductor wafer, a photomask, a reticle, a flat panel display, and a biological material.

23. The system according to claim 15, wherein said speed of relative movement is calculated by measuring an elapsed time between two outputted scanning axis signals.

24. The system according to claim 23, wherein said two outputted scanning axis signals are consecutive.

25. The system according to claim 15, wherein said scanner resolution is determined based on at least one factor selected from the group consisting of said speed of relative movement, a surface structure of said inspection article, and a surface material of said inspection article.

26. The system according to claim 15, wherein said new scan line generation is delayed based on said scanning axis error.

27. The system according to claim 15, wherein said new scan line generation is advanced based on said scanning axis error.

28. The system according to claim 15, wherein said scanner comprises:

a light source outputting a light beam; and an acousto-optic deflector receiving said light beam and deflecting said light beam to scan said surface of said inspection article;

wherein said controller comprises an RF generator controlling said acousto-optic deflector to perform said generating and said shifting.

29. The system according to claim 28, wherein said controller further comprises:

a cross-scanning axis correction system to provide inputs to said RF generator to perform said generating; and a scanning axis correction system to provide further inputs to said RF generator to perform said shifting.

30. The system according to claim 29, wherein said cross-scanning axis correction system comprises:

a cross-scanning axis static position error correction table as one of said static position error correction tables;

a counter for outputting a count in response to said jitter signal; and a summarizer receiving outputs of said counter and said cross-scanning axis static position error correction table and providing a signal to said RF generator to perform said generating.

31. The system according to claim 30, wherein said cross-scanning axis correction system further comprises a look-up table receiving an output of said summarizer and providing said signal to said RF generator to perform said generating.

32. The system according to claim 29, wherein said scanning axis correction system comprises:

a scanning axis static position error correction table as one of said static position error correction tables;

a velocity estimator performing said determining said speed of relative movement;

a resolution multiplier providing scan line resolution information; and a module responsive to outputs of said scanning axis static position error correction table, said velocity estimator, and said resolution multiplier and providing a signal to said RF generator to perform said shifting.

* * * * *